US008642679B2

(12) United States Patent
Tanaka et al.

(10) Patent No.: US 8,642,679 B2
(45) Date of Patent: Feb. 4, 2014

(54) DENTAL CEMENT COMPOSITION

(75) Inventors: Koji Tanaka, Itabashi-ku (JP); Hideki Yarimizu, Itabashi-ku (JP); Hisashi Nakaseko, Itabashi-ku (JP)

(73) Assignee: GC Corporation, Tokyo (JP)

( * ) Notice: Subject to any disclaimer, the term of this patent is extended or adjusted under 35 U.S.C. 154(b) by 161 days.

(21) Appl. No.: 12/552,770

(22) Filed: Sep. 2, 2009

(65) Prior Publication Data

US 2010/0068678 A1 Mar. 18, 2010

(30) Foreign Application Priority Data

Sep. 12, 2008 (JP) ................................. 2008-235095

(51) Int. Cl.
*A61K 6/08* (2006.01)
(52) U.S. Cl.
USPC ............ 523/116; 523/115; 524/178; 524/494
(58) Field of Classification Search
USPC .................. 523/116, 117, 115; 524/178, 494
See application file for complete search history.

(56) References Cited

U.S. PATENT DOCUMENTS

| 2,669,550 | A | * | 2/1954 | Brown | 525/368 |
| 2,760,431 | A | * | 8/1956 | Beatty | 101/457 |
| 3,814,717 | A | * | 6/1974 | Wilson et al. | 433/228.1 |
| 3,929,493 | A | * | 12/1975 | Lee et al. | 106/35 |
| 4,043,327 | A | * | 8/1977 | Potter et al. | 602/8 |
| 4,123,416 | A | * | 10/1978 | Potter et al. | 523/111 |
| 4,137,086 | A | * | 1/1979 | Potter et al. | 501/73 |
| 4,183,759 | A | * | 1/1980 | Epstein | 106/38.2 |
| 4,527,979 | A | * | 7/1985 | McLean et al. | 433/228.1 |
| 4,647,600 | A | * | 3/1987 | Kawahara et al. | 523/116 |
| 4,652,593 | A | * | 3/1987 | Kawahara et al. | 523/116 |
| 4,738,722 | A | * | 4/1988 | Ibsen et al. | 106/35 |
| 4,746,686 | A | * | 5/1988 | Waller | 522/14 |
| 4,758,612 | A | * | 7/1988 | Wilson et al. | 524/5 |
| RE33,100 | E | * | 10/1989 | Ibsen et al. | 106/35 |
| 4,872,936 | A | * | 10/1989 | Engelbrecht | 156/307.3 |
| 5,063,257 | A | * | 11/1991 | Akahane et al. | 523/116 |
| 5,141,560 | A | * | 8/1992 | Combe et al. | 106/35 |
| 5,154,613 | A | * | 10/1992 | Cohen | 433/228.1 |
| 5,844,019 | A | | 12/1998 | Kato | |
| 2006/0247330 | A1 | | 11/2006 | Takano et al. | |
| 2009/0050015 | A1 | * | 2/2009 | Hermansson et al. | 106/35 |
| 2010/0068678 | A1 | * | 3/2010 | Tanaka et al. | 433/224 |

FOREIGN PATENT DOCUMENTS

| BE | 905423 A * | 12/1986 |
| JP | 2002-220314 | 8/2002 |
| WO | WO 0173265 A1 * | 10/2001 |
| WO | WO 2004098541 A1 * | 11/2004 |
| WO | WO 2009025599 A1 * | 2/2009 |

OTHER PUBLICATIONS

U.S. Appl. No. 12/835,216, filed Jul. 13, 2010, Yarimizu, et al.
Extended European Search Report issued Nov. 24, 2009, in European Patent Application No. 09011098.2-1219.

* cited by examiner

*Primary Examiner* — James J Seidleck
*Assistant Examiner* — Peter A Salamon
(74) *Attorney, Agent, or Firm* — Oblon, Spivak, McClelland, Maier & Neustadt, L.L.P.

(57) ABSTRACT

To provide a dental glass ionomer cement for a sealer to be used for sealing a gap between a gutta-percha point filled in a root canal in a dental root canal treatment and a root canal wall, with a prolonged setting time and with sufficient setting property even in a root canal having much water content, the dental cement for a sealer includes a polymer of $\alpha\text{-}\beta$ unsaturated carboxylic acid, oxide powder capable of reacting with the polymer of $\alpha\text{-}\beta$ unsaturated carboxylic acid, and water, and further includes an organic acid salt of metal selected from Mg, Ca, and Sr and/or a hydroxide of metal selected from Mg, Ca, and Sr.

17 Claims, No Drawings

DENTAL CEMENT COMPOSITION

CROSS-REFERENCE TO RELATED APPLICATIONS

This application claims priority to Japanese Patent Application No. 2008-235095, filed on Sep. 12, 2008.

BACKGROUND OF THE INVENTION

1. Field of the Invention

The present invention relates to a cement for sealer used for sealing a gap between a gutta-percha point, which is filled in a root canal in a dental root canal treatment, and a root canal wall.

2. Description of the Conventional Art

A root canal treatment is widely carried out. In the root canal treatment, a stable material is filled in a root canal after dental pulp extraction so as to seal a void in the root canal, and thus infection routes between the root canal and periodontal tissue and between the root canal and an oral cavity are blocked. A most widely used method in the root canal treatment includes the steps of filling a thin needle-shaped root canal filler called a gutta-percha point mainly including gutta-percha and zinc oxide in a root canal after dental pulp extraction, and sealing the root canal with a dental cement. At this time, it is necessary to precisely fill the gutta-percha point in the root canal, but the gutta-percha point has insufficient adhesivity to a root canal wall. Thus, in order to increase sealability, a material called a root canal filling sealer is applied on the gutta-percha point, and then the gutta-percha point is filled in the root canal, whereby a gap between the root canal wall and the gutta-percha point is plugged.

As for the root canal filling sealer, a material mainly including zinc oxide and eugenol is widely used. However, the zinc oxide/eugenol-based root canal filling sealer composition can plug the gap between the root canal wall and the gutta-percha point, but has low adhesivity to both the root canal wall and the gutta-percha point. Therefore, there is a problem in sealability to the root canal in a clinical treatment. Further, the eugenol has a toxic action for an organism, and thus there is a problem in safety for a human body.

On the other hand, as for a root canal filling sealer composition using a glass ionomer cement widely used for a dental filling treatment or adhesion, for example, Japanese Patent Application Laid-Open No. 2002-220314 discloses a root canal filling sealer composition including powder for a root canal filling glass ionomer-based sealer, which is made by blending fluoroaluminosilicate glass powder, a polymer not reacting with polycarboxylic acid and/or an inorganic filler not reacting with polycarboxylic acid, and polycarboxylic acid. The root canal filling sealer composition including the powder for a root canal filling glass ionomer-based sealer and the polycarboxylic acid has an object that it can be easily removed from the root canal when the root canal needs to be re-treated.

A dental glass ionomer cement mainly includes a polymer of α-β unsaturated carboxylic acid, oxide powder capable of reacting with the polymer of α-β unsaturated carboxylic acid, and water. Since a sealer composition using the dental glass ionomer cement adheres to both a tooth and a gutta-percha point, the sealer composition has excellent sealability of a root canal, and also is excellent in safety because of having high bioaffinity for a human body. However, the dental glass ionomer cement is set rapidly in general. Thus, in order to use the dental glass ionomer cement for a sealer application, it is necessary to decrease a setting speed so as to secure a sufficient working time. As for a method for decreasing the setting speed, for example, a method by adding a component not reacting with acid and a glass as disclosed in Japanese Patent Application Laid-Open No. 2002-220314, and a method by decreasing the content of acid and/or a glass so as to decrease the amount of ionic bond, can be used. However, when a dental glass ionomer cement is contacted with much water content in a setting process, a metal ion concentration which is a main factor for a setting reaction is decreased, so there is a problem that setting property is decreased. Therefore, when such the root canal filling sealer composition with the prolonged setting speed is used under a condition with much water content such as a dentin in a root canal, setting is hindered and, as a result, there is a problem that a root canal cannot be sealed sufficiently.

SUMMARY OF THE INVENTION

Problem to be Solved by the Invention

The present invention is directed to provide a dental glass ionomer cement for a sealer with a prolonged setting time, which has sufficient setting property in a root canal even with much water content.

Means for Solving the Problem

The present inventors carried out earnest works to solve the aforementioned problems and, as a result, they found out the followings to complete the present invention. When an organic acid salt of metal selected from Mg, Ca and Sr and/or a hydroxide of metal selected from Mg, Ca and Sr are added in a dental cement including a polymer of α-β unsaturated carboxylic acid, oxide powder capable of reacting with the polymer of α-β unsaturated carboxylic acid, and water, these components sustainably releases metal ions in a case that excessive water content exists, so as to prevent decreasing of a metal ion concentration. Thus, a setting reaction of the cement can continue even under a condition with much water content.

That is, the present invention is a dental cement for a sealer including a polymer of α-β unsaturated carboxylic acid, oxide powder capable of reacting with the polymer of α-β unsaturated carboxylic acid, and water, wherein the dental cement further includes an organic acid salt of metal selected from Mg, Ca and Sr and/or a hydroxide of metal selected from Mg, Ca and Sr.

Effect of the Invention

A cement for a sealer according to the present invention can sufficiently seal a root canal when being used together with a root canal filling material even under a condition with much water content such as an inside of a root canal.

DETAILED DESCRIPTION OF PREFERRED EMBODIMENT

A polymer of α-β unsaturated carboxylic acid in a present invention is a polymer of α-β unsaturated monocarboxylic acid or α-β unsaturated dicarboxylic acid. For example, the polymer is a homopolymer or a copolymer of acrylic acid, methacrylic acid, 2-chloroacrylic acid, aconitic acid, mesaconic acid, maleic acid, itaconic acid, fumaric acid, glutaconic acid, citraconic acid, or the like. The copolymer can be a copolymer of α-β unsaturated carboxylic acids themselves, or can be a copolymer of α-β unsaturated carboxylic acid and a material copolymerizable with the α-β unsaturated carboxylic acid. In this case, the ratio of α-β unsaturated carboxylic acid is preferably 50% or more. As for the copolymerizable material, for example, acrylamide, acrylonitrile, methacrylic ester, acrylates, vinyl chloride, allyl chloride, and vinyl acetate, can be used. Among these polymers of α-β unsaturated carboxylic acid, a homopolymer or copolymer of acrylic acid or maleic acid is particularly preferable.

The polymer of α-β unsaturated carboxylic acid is a component which can be reacted with oxide powder described below and set. If the polymer having the weight average molecular weight of less than 5,000 is used, the strength of the set material is low, and thus there is a problem in durability. Further, adhesiveness to a tooth structure is also decreased. If the polymer having the weight average molecular weight of more than 40,000 is used, consistency of the cement composition when being kneaded is too high, and thus it is very difficult to knead the cement composition. Therefore, the average molecular weight of the α-β unsaturated carboxylic acid polymer used in the present invention is ranged from 5,000 to 40,000.

As for the oxide powder capable of reacting with the polymer of α-β unsaturated carboxylic acid, materials conventionally used for a dental cement can be used. For example, fluoroaluminosilicate powder used for a glass ionomer cement can be used. As for the fluoroaluminosilicate powder, aluminosilicate glass powder, which includes $Al^{3+}$, $Si^{4+}$, $F^-$, and $O^{2-}$ as main components and further includes $Sr^{2+}$ and/or $Ca^{2+}$, is preferable. Particularly, such ratios of the main components with respect to the total weight of the glass that $Al^{3+}$ is 10 to 21% by weight, $Si^{4+}$ is 9 to 21% by weight, $F^-$ is 1 to 20% by weight, and the total of $Sr^{2+}$ and $Ca^{2+}$ is 10 to 34% by weight are preferable.

As for the organic acid salt of metal selected from Mg, Ca, and Sr to be used in the present invention, an organic acid salt selected from methacrylic acid, acrylic acid, succinic acid, oxalic acid, tartaric acid, malic acid, citric acid, glycolic acid, malonic acid, pyruvic acid, oleic acid, stearic acid, fumaric acid, benzoic acid, aminobenzoic acid, linolic acid, acetic acid, adipic acid, lauric acid, palmitic acid, lactic acid, montanic acid, behenic acid, terephthalic acid, glyceric acid, propionic acid, and the like can be used. For example, magnesium methacrylate, calcium methacrylate, strontium methacrylate, magnesium acrylate, calcium acrylate, strontium acrylate, magnesium succinate, calcium succinate, strontium succinate, magnesium oxalate, calcium oxalate, strontium oxalate, calcium tartrate, magnesium tartrate, strontium tartrate, magnesium malate, calcium malate, strontium malate, magnesium citrate, calcium citrate, strontium citrate, magnesium glycolate, calcium glycolate, strontium glycolate, magnesium malonate, calcium malonate, strontium malonate, magnesium pyruvate, calcium pyruvate, strontium pyruvate, magnesium oleate, calcium oleate, strontium oleate, magnesium stearate, calcium stearate, strontium stearate, magnesium fumarate, calcium fumarate, strontium fumarate, magnesium benzoate, calcium benzoate, strontium benzoate, magnesium linolate, calcium linolate, strontium linolate, magnesium acetate, calcium acetate, strontium acetate, magnesium adipate, calcium adipate, strontium adipate, magnesium laurate, calcium laurate, strontium laurate, magnesium palmitate, calcium palmitate, strontium palmitate, magnesium lactate, calcium lactate, strontium lactate, magnesium montanate, calcium montanate, strontium montanate, magnesium behenate, calcium behenate, strontium behenate, magnesium terephthalate, calcium terephthalate, strontium terephthalate, magnesium glycerate, calcium glycerate, strontium glycerate, magnesium propionate, calcium propionate, and strontium propionate, can be used. Two or more of these organic acid salts can be combined to be used. Among those, when the organic acid salts is tartrate of metal selected from Mg, Ca, and Sr, solubility to water is proper. Further, since these tartrates of metal have a sustainable release property of metal ions in a proper amount for preventing setting hindrance by water while keeping a long working time, thus it is preferable. Particularly, calcium tartrate is the most preferable from the viewpoints of a working time, the strength of a final set body, and safety for a human body.

As for the hydroxide of metal selected from Mg, Ca, and Sr, for example, magnesium hydroxide, a calcium hydroxide, and strontium hydroxide, can be used, and these can be combined to be used.

The organic acid salt of metal selected from Mg, Ca, and Sr and the hydroxide of metal selected from Mg, Ca, and Sr can be an anhydrous salt or include crystal water. Among those, since the hydroxide of metal selected from Mg, Ca, and Sr has a high atomic weight, high X-ray imaging property can be given, and thus it is preferable. Particularly, strontium hydroxide is the most preferable from the viewpoints of a working time, the strength of a final set body, and the X-ray imaging property of a final set body.

When the cement for a sealer according to the present invention includes powder not reacting with the polymer of α-β unsaturated carboxylic acid, adhesive strength to a tooth can be adjusted and radiopacity can be given to the powder component so as to increase the X-ray imaging property, so it is preferable. As for the powder not reacting with the polymer of α-β unsaturated carboxylic acid, for example, quartz, colloidal silica, feldspar, alumina, strontium glass, barium glass, borosilicate glass, kaolin, talc, calcium carbonate, titania, barium sulfate, zirconia, bismuth subcarbonate, iodoform, calcium tungstate, and the like can be used. Further, a composite filler made by pulverizing a prepolymerized filler including an inorganic particle can be used. Of course, these can be mixed to be used.

The cement for a sealer according to the present invention can be properly blended with a coloring agent, an ultraviolet absorber, an antibacterial agent, and a perfume.

EXAMPLE

Example

The present invention will be described in detail below with examples, but the present invention is not limited to these examples.

[Preparation of Fluoroaluminosilicate Glass as Oxide Powder]

Blending amounts of fluoroaluminosilicate glass powders I, II, and III are illustrated in Table 1.

TABLE 1

|  | Fluoroaluminosilicate glass powders | | |
|---|---|---|---|
|  | I | II | III |
| Aluminium oxide (g) | 21 | 23 | 22 |
| Silicon deoxide (g) | 44 | 41 | 43 |
| Calcium fluoride (g) | 12 | 10 | 12 |
| Calcium phosphate (g) | 14 | 13 | 15 |
| Strontium carbonate (g) | 9 | 13 | 8 |

The fluoroaluminosilicate glass powders I and III were obtained by fully mixing raw materials, holding the mixture in a high temperature electric furnace at 1200° C. for 5 hours so as to melt a glass, cooling the mixture after melting the glass, pulverizing the product using a ball mill for 10 hours, and sieving the pulverized product with a 200 mesh sieve (ASTM). The fluoroaluminosilicate glass powder II was obtained by a similar process to that of the fluoroaluminosilicate glass powders I and III except the glass is melted at 1100° C.

[Preparation of a Cement for a Sealer]

Blending amounts of a two-paste type cement for a sealer and a powder and liquid type cement for a sealer used in each example and comparative example, working times measured by the following methods, and test results of compressive strength and setting property are shown in Tables 2 and 3.

TABLE 2

| | | | Example 1 | Example 2 | Example 3 | Example 4 | Example 5 | Example 6 |
|---|---|---|---|---|---|---|---|---|
| First Paste | Oxide powders | Fluoroaluminosilicate glass powder I | 40 | | | 45 | 45 | |
| | | Fluoroaluminosilicate glass powder II | | 40 | | | | 40 |
| | | Fluoroaluminosilicate glass powder III | | | 35 | | | |
| | Powder not reacting with acid | Barium sulfate | 10 | | 16 | 10 | | 15 |
| | | Quartz | | 10 | | | 10 | |
| | Viscosity regulator | Hydroxypropyl cellulose | 2 | | 2 | 2 | | 2 |
| | | Sodium Carboxymethyl cellulose | | 2 | | | 2 | |
| | | Silica fine powder | 1 | 1 | 1 | 1 | 1 | 1 |
| | | Alumina fine powder | 1 | 1 | 1 | 1 | 1 | 1 |
| | Water | | 38.997 | 35.997 | 37.997 | 30.997 | 28.997 | 35.997 |
| | Organic acid salt and/or hydroxide of metal selected from Mg, Ca, and Sr | Calcium tartrate | 7 | | 7 | 10 | | 5 |
| | | Calcium hydroxide | | 10 | | | 12 | |
| | Pigment | Iron oxide | 0.003 | 0.003 | 0.003 | 0.003 | 0.003 | 0.003 |
| | Total | | 100 | 100 | 100 | 100 | 100 | 100 |
| Second Paste | α-β unsaturated carboxylic acid polymer | Polyacrylic acid | 20 | 30 | 30 | 20 | 25 | 25 |
| | Powder not reacting with acid | Barium sulfate | 35 | 25 | 40 | 40 | 35 | 35 |
| | | Quartz | 5 | 5 | | | | 5 |
| | Water | | 40 | 40 | 30 | 40 | 40 | 35 |
| | Total | | 100 | 100 | 100 | 100 | 100 | 100 |
| | Working time | | 35 minutes | 18 minutes and 30 seconds | 20 minutes | 33 minutes | 18 minutes | 17 minutes and 30 seconds |
| | Compressive Strength [MPa] | | 38 | 46 | 40 | 41 | 52 | 49 |
| | Setting Property | | Set | Set | Set | Set | Set | Set |

| | | | Example 7 | Example 8 | Example 9 | Comparative example 1 | Comparative example 2 |
|---|---|---|---|---|---|---|---|
| First Paste | Oxide powders | Fluoroaluminosilicate glass powder I | | | | | |
| | | Fluoroaluminosilicate glass powder II | 45 | | | | |
| | | Fluoroaluminosilicate glass powder III | | 40 | 45 | 45 | 55 |
| | Powder not reacting with acid | Barium sulfate | | 15 | | 15 | |
| | | Quartz | 5 | | 5 | | 5 |
| | Viscosity regulator | Hydroxypropyl cellulose | | 2 | | 2 | |
| | | Sodium Carboxymethyl cellulose | 2 | | 2 | | 2 |
| | | Silica fine powder | 1 | 1 | 1 | 1 | 1 |
| | | Alumina fine powder | 1 | 1 | 1 | 1 | 1 |
| | Water | | 35.997 | 35.997 | 35.997 | 35.997 | 35.997 |
| | Organic acid salt and/or hydroxide of metal selected from Mg, Ca, and Sr | Calcium tartrate | 10 | | | | |
| | | Calcium hydroxide | | 5 | 10 | | |
| | Pigment | Iron oxide | 0.003 | 0.003 | 0.003 | 0.003 | 0.003 |
| | Total | | 100 | 100 | 100 | 100 | 100 |

TABLE 2-continued

| | | | | | | | |
|---|---|---|---|---|---|---|---|
| Second Paste | α-β unsaturated carboxylic acid polymer | Polyacrylic acid | 20 | 25 | 25 | 25 | 25 |
| | Powder not reacting with acid | Barium sulfate | 35 | 35 | 35 | 35 | 35 |
| | | Quartz | 5 | | 5 | | 5 |
| | Water | | 40 | 40 | 35 | 40 | 35 |
| | Total | | 100 | 100 | 100 | 100 | 100 |
| | Working time | | 19 minutes | 18 minutes | 17 minutes and 30 seconds | 18 minutes | 17 minutes and 30 seconds |
| | Compressive Strength [MPa] | | 40 | 48 | 51 | 10 | 16 |
| | Setting Property | | Set | Set | Set | Insufficiently set | Insufficiently set |

Weight ratio of First Paste and Second Paste = 1.0 g/1.8 g

TABLE 3

| | | | Example 10 | Example 11 | Example 12 | Example 13 | Example 14 |
|---|---|---|---|---|---|---|---|
| Powder | Oxide powders | Fluoroaluminosilicate glass powder I | 65 | | | 55 | 55 |
| | | Fluoroaluminosilicate glass powder II | | 70 | | | |
| | | Fluoroaluminosilicate glass powder III | | | 60 | | |
| | Fillers not reacting with acid | Barium sulfate | 24.997 | 9.997 | 24.997 | 34.997 | 24.997 |
| | | Quartz | | 10 | 5 | | 5 |
| | Organic acid salt and/or hydroxide of metal selected from Mg, Ca, and Sr | Calcium tartrate | 10 | | 10 | 10 | |
| | | Calcium hydroxide | | 10 | | | 15 |
| | Pigment | Iron oxide | 0.003 | 0.003 | 0.003 | 0.003 | 0.003 |
| | Total | | 100 | 100 | 100 | 100 | 100 |
| Liquid | α-β unsaturated carboxylic acid polymer | Polyacrylic acid | 30 | 30 | 25 | 25 | 20 |
| | Viscosity regulator | Hydroxypropyl cellulose | 2 | 2 | 3 | 3 | 4 |
| | | Silica fine powder | 1 | 1 | 1 | 2 | 2 |
| | | Alumina fine powder | 1 | 2 | 2 | 2 | 2 |
| | Water | | 66 | 65 | 69 | 68 | 72 |
| | Total | | 100 | 100 | 100 | 100 | 100 |
| | Working time | | 15 minutes | 16 minutes | 20 minutes | 26 minutes | 31 minutes |
| | Compressive Strength [MPa] | | 61 | 60 | 56 | 52 | 50 |
| | Setting property | | Set | Set | Set | Set | Set |

| | | | Example 15 | Example 16 | Comparative example 3 | Comparative example 4 |
|---|---|---|---|---|---|---|
| Powder | Oxide powders | Fluoroaluminosilicate glass powder I | | | | |
| | | Fluoroaluminosilicate glass powder II | 55 | | 65 | |
| | | Fluoroaluminosilicate glass powder III | | 50 | | 65 |
| | Fillers not reacting with acid | Barium sulfate | 29.997 | 34.997 | 29.997 | 34.997 |
| | | Quartz | 5 | | 5 | |
| | Organic acid salt and/or hydroxide of metal selected from Mg, Ca, and Sr | Calcium tartrate | 10 | | | |
| | | Calcium hydroxide | | 15 | | |
| | Pigment | Iron oxide | 0.003 | 0.003 | 0.003 | 0.003 |
| | Total | | 100 | 100 | 100 | 100 |
| Liquid | α-β unsaturated carboxylic acid polymer | Polyacrylic acid | 20 | 20 | 20 | 20 |
| | Viscosity regulator | Hydroxypropyl cellulose | 6 | 4 | 6 | 4 |
| | | Silica fine powder | 2 | 2 | 2 | 2 |
| | | Alumina fine powder | 3 | 3 | 3 | 3 |
| | Water | | 69 | 71 | 69 | 71 |
| | Total | | 100 | 100 | 100 | 100 |

TABLE 3-continued

| Working time | 32 minutes | 35 minutes | 32 minutes | 35 minutes |
|---|---|---|---|---|
| Compressive Strength [MPa] | 49 | 49 | 13 | 12 |
| Setting property | Set | Set | Insufficiently set | Insufficiently set |

Powder/liquid ratio = 4.0 g/1.0 g

[Working Time]

0.05 mL of a kneaded cement for a sealer was taken on a glass plate, and a load of 120 g was applied to the cement after 180 seconds from the beginning of kneading. Then, the load is removed after 10 minutes from the beginning of kneading, and an average of the largest diameter and the smallest diameter of the pressed cement was made to be a consistency. Timing for applying the load is made to be later gradually, and the time when the value of the consistency is decreased 10% was made to be a working time.

[Compressive Strength]

The sealability of a cement for a sealer depends on the strength of the cement itself, so a compressive strength was measured to evaluate the sealability. A kneaded cement for a sealer was filled into a metal mold having an inner diameter of 4 mm and a length of 6 mm so as to obtain a cylindrical set body. After 120 seconds from the finishing of kneading, the set body was held for 1 hour in a thermo-hygrostat at 37° C. and a relative humidity of 100%. Then, an obtained test piece was soaked in distilled water at 37° C. for 23 hours, and subjected to a compressive test at a crosshead speed of 1.0 mm/min. using a universal testing machine (product name: AUTOGRAPH, produced by SHIMAZU CORPORATION).

[Setting Property]

A kneaded cement for a sealer was filled into a mold having an inner diameter of 10 mm and a height of 2 mm, and held for 1 hour in a thermo-hygrostat at 37° C. and a relative humidity of 100% after 120 seconds from the finishing of kneading. Then, an obtained test piece was soaked in distilled water at 37° C. for 23 hours. A Vicat tester having a mass of 10 g and an end diameter of 2 mm was made to slowly fall on a horizontal face of the kneaded material, and a mark of the needle was confirmed visually. Those which had no mark was determined as "Set", and the those which had the mark was determined as "Insufficiently set".

Clearly from Tables 2 and 3, since the cements for a sealer of each example included the inorganic filler not reacting with polycarboxylic acid in addition to the fluoroaluminosilicate glass powder, it was confirmed that the working time of the cement was approximately 20 minutes, which was proper for filling a root canal, similar to the working time of the cement for a sealer of each comparative example.

Further, it was confirmed that the compressive strength of the cement for a sealer of each example was fully higher than that of the cement of each comparative example. Considering the condition in a root canal with much water content, the compressive strength was measured after the test piece, which was obtained after being held for 1 hour in a thermo-hygrostat at 37° C. and a relative humidity of 100% after 120 seconds from the finishing of kneading, was soaked in distilled water at 37° C. for 23 hours. Since the cement of each comparative example did not include an organic acid salt of metal selected from Mg, Ca and Sr and/or a hydroxide of metal selected from Mg, Ca and Sr, the cement was influenced by water so as to make the compressive strength insufficient. That is, the cement for a sealer of each example had high sealability to a root canal.

Furthermore, it was confirmed that the setting property of the cement for a sealer of each example was fully higher than that of the cement of each comparative example. Considering the condition in a root canal with much water content, the setting property was measured after the test piece, which was obtained after being held for 1 hour in a thermo-hygrostat at 37° C. and a relative humidity of 100% after 120 seconds from the finishing of kneading, was soaked in distilled water at 37° C. for 23 hours. Since the cement of each comparative example did not include an organic acid salt of metal selected from Mg, Ca and Sr and/or a hydroxide of metal selected from Mg, Ca and Sr, the cement was influenced by water so as to make the setting property insufficient.

Therefore, the cement for a sealer according to the present invention can be sufficiently used even in a root canal with much water content.

What is claimed is:

1. A dental glass ionomer cement comprising:
   a first component comprising a fluoroaluminosilicate glass powder and a powder which does not react with a polymer of α-β unsaturated carboxylic acid, and
   a second component comprising a polymer of α-β unsaturated carboxylic acid, water and a powder which does not react with a polymer of α-β unsaturated carboxylic acid,
   wherein the first component further comprises:
   an organic acid salt of metal selected from the group consisting of Mg, Ca, and Sr; and/or
   a hydroxide of metal selected from the group consisting of Mg, Ca, and Sr.

2. The dental glass ionomer cement for a sealer as claimed in claim 1, wherein the organic acid salt of metal selected from the group consisting of Mg, Ca, and Sr is one or more kinds of organic acid salts selected from the group consisting of methacrylic acid, acrylic acid, succinic acid, oxalic acid, tartaric acid, malic acid, citric acid, glycolic acid, malonic acid, pyruvic acid, oleic acid, stearic acid, fumaric acid, benzoic acid, aminobenzoic acid, linolic acid, acetic acid, adipic acid, lauric acid, palmitic acid, lactic acid, montanic acid, behenic acid, terephthalic acid, glyceric acid, and propionic acid.

3. The dental glass ionomer cement for a sealer as claimed in claim 1, wherein the organic acid salt of metal selected from the group consisting of Mg, Ca, and Sr is one or more kinds selected from the group consisting of magnesium methacrylate, calcium methacrylate, strontium methacrylate, magnesium acrylate, calcium acrylate, strontium acrylate, magnesium succinate, calcium succinate, strontium succinate, magnesium oxalate, calcium oxalate, strontium oxalate, calcium tartrate, magnesium tartrate, strontium tartrate, magnesium malate, calcium malate, strontium malate, magnesium citrate, calcium citrate, strontium citrate, magnesium glycolate, calcium glycolate, strontium glycolate, magnesium malonate, calcium malonate, strontium malonate, magnesium pyruvate, calcium pyruvate, strontium pyruvate, magnesium oleate, calcium oleate, strontium oleate, magnesium stearate, calcium stearate, strontium stearate, magnesium fumarate, calcium fumarate, strontium fumarate, magnesium benzoate, calcium benzoate, strontium benzoate, magnesium linolate, calcium linolate, strontium linolate, magnesium acetate, calcium acetate, strontium acetate, magnesium adipate, calcium adipate, strontium adipate, magnesium laurate, calcium laurate, strontium laurate, magnesium palmitate, calcium palmitate, strontium palmitate, magnesium lactate, calcium lactate, strontium lactate, magnesium montanate, calcium montanate, strontium montanate, magnesium behenate, calcium behenate, strontium behenate, magnesium terephthalate, calcium terephthalate, strontium terephthalate, magnesium glycerate, calcium glycerate, strontium glycerate, magnesium propionate, calcium propionate, and strontium propionate.

4. The dental glass ionomer cement for a sealer as claimed in claim 2, wherein the organic acid salt of metal selected from the group consisting of Mg, Ca, and Sr is one or more kinds selected from the group consisting of magnesium methacrylate, calcium methacrylate, strontium methacrylate, magnesium acrylate, calcium acrylate, strontium acrylate, magnesium succinate, calcium succinate, strontium succinate, magnesium oxalate, calcium oxalate, strontium oxalate, calcium tartrate, magnesium tartrate, strontium tartrate, magnesium malate, calcium malate, strontium malate, magnesium citrate, calcium citrate, strontium citrate, magnesium glycolate, calcium glycolate, strontium glycolate, magnesium malonate, calcium malonate, strontium malonate, magnesium pyruvate, calcium pyruvate, strontium pyruvate, magnesium oleate, calcium oleate, strontium oleate, magnesium stearate, calcium stearate, strontium stearate, magnesium fumarate, calcium fumarate, strontium fumarate, magnesium benzoate, calcium benzoate, strontium benzoate, magnesium linolate, calcium linolate, strontium linolate, magnesium acetate, calcium acetate, strontium acetate, magnesium adipate, calcium adipate, strontium adipate, magnesium laurate, calcium laurate, strontium laurate, magnesium palmitate, calcium palmitate, strontium palmitate, magnesium lactate, calcium lactate, strontium lactate, magnesium montanate, calcium montanate, strontium montanate, magnesium behenate, calcium behenate, strontium behenate, magnesium terephthalate, calcium terephthalate, strontium terephthalate, magnesium glycerate, calcium glycerate, strontium glycerate, magnesium propionate, calcium propionate, and strontium propionate.

5. The dental glass ionomer cement for a sealer as claimed in claim 1, wherein the cement has a setting time of from 15 to 35 minutes.

6. The dental glass ionomer cement for a sealer as claimed in claim 1, wherein the organic acid salt of metal and/or the hydroxide of metal is an anhydrous salt.

7. The dental glass ionomer cement for a sealer as claimed in claim 1, wherein the organic acid salt of metal and/or the hydroxide of metal comprises crystal water.

8. The dental glass ionomer cement for a sealer as claimed in claim 1, wherein the hydroxide of metal is strontium hydroxide.

9. The dental glass ionomer cement for a sealer as claimed in claim 1, wherein the powder which does not react with the polymer of α-β unsaturated carboxylic acid is at least one selected from the group consisting of quartz, colloidal silica, feldspar, alumina, strontium glass, barium glass, borosilicate glass, kaolin, talc, calcium carbonate, titania, barium sulfate, zirconia, bismuth subcarbonate, iodoform and calcium tungstate.

10. The dental glass ionomer cement for a sealer as claimed in claim 1, wherein the cement further comprises a composite filler made by pulverizing a prepolymerized filler comprising an inorganic particle.

11. The dental glass ionomer cement for a sealer as claimed in claim 1, wherein said cement is mixed with a coloring agent, an ultraviolet absorber, an antibacterial agent, and/or a perfume.

12. The dental glass ionomer cement of claim 1, wherein the first component comprises at least one organic acid salt of metal selected from the group consisting of Mg, Ca, and Sr.

13. The dental glass ionomer cement of claim 1, wherein the first component comprises a hydroxide of metal selected from the group consisting of Mg, Ca, and Sr.

14. The dental glass ionomer cement of claim 1, wherein the first component comprises
   at least one organic acid salt of metal selected from the group consisting of Mg, Ca, and Sr, and
   a hydroxide of metal selected from the group consisting of Mg, Ca, and Sr.

15. A sealer comprising the dental glass ionomer cement of claim 1.

16. A cured dental glass ionomer cement of claim 1.

17. The dental glass ionomer cement of claim 1 wherein the first component and the second component react.

* * * * *